United States Patent
Pruvost et al.

(10) Patent No.: US 10,611,854 B2
(45) Date of Patent: Apr. 7, 2020

(54) DEGUMMING METHOD

(71) Applicants: ALGOSOURCE, Saint Nazaire (FR); UNIVERSITE DE NANTES, Nantes (FR)

(72) Inventors: Jérémy Pruvost, Saint Brevin les Pins (FR); Pascal Jaouen, Le Pouliguen (FR); Luc Marchal, Saint Nazaire (FR); Sébastien Jubeau, Guerande (FR); Joël Fleurence, Fay de Bretagne (FR)

(73) Assignees: ALGOSOURCE, Saint Nazaire (FR); UNIVERSITE DE NANTES, Nantes (FR)

( * ) Notice: Subject to any disclaimer, the term of this patent is extended or adjusted under 35 U.S.C. 154(b) by 47 days.

(21) Appl. No.: 15/518,926

(22) PCT Filed: Oct. 13, 2015

(86) PCT No.: PCT/EP2015/073689
§ 371 (c)(1),
(2) Date: Apr. 13, 2017

(87) PCT Pub. No.: WO2016/059058
PCT Pub. Date: Apr. 21, 2016

(65) Prior Publication Data
US 2017/0233499 A1     Aug. 17, 2017

(30) Foreign Application Priority Data

Oct. 13, 2014    (FR) ...................................... 14 59796

(51) Int. Cl.
| | | |
|---|---|---|
| C08B 37/00 | (2006.01) | |
| C12N 1/12 | (2006.01) | |
| A61K 8/73 | (2006.01) | |
| C12N 13/00 | (2006.01) | |
| C12P 19/04 | (2006.01) | |
| C12N 1/06 | (2006.01) | |
| A23L 29/269 | (2016.01) | |
| A61Q 19/00 | (2006.01) | |
| A61K 8/9706 | (2017.01) | |

(52) U.S. Cl.
CPC ........ *C08B 37/0003* (2013.01); *A23L 29/269* (2016.08); *A61K 8/73* (2013.01); *A61K 8/9706* (2017.08); *A61Q 19/00* (2013.01); *C12N 1/066* (2013.01); *C12N 1/12* (2013.01); *C12N 13/00* (2013.01); *C12P 19/04* (2013.01); *A61K 2800/10* (2013.01); *A61K 2800/805* (2013.01)

(58) Field of Classification Search
CPC .......... C12N 1/066; C12N 1/12; C08B 37/003
See application file for complete search history.

(56) References Cited

U.S. PATENT DOCUMENTS

| 4,960,697 A | 10/1990 | Johal et al. |
|---|---|---|
| 2012/0202768 A1* | 8/2012 | Coragliotti .............. C12P 19/04 514/54 |

FOREIGN PATENT DOCUMENTS

| EP | 0 311 496 A2 | 4/1989 |
|---|---|---|
| WO | 83/03738 A1 | 11/1983 |

OTHER PUBLICATIONS

Patel Kumar et al., "Separation and Fractionation of Exopolysaccharides From Porphyridium Cruentum", Bioresource Technology, vol. 145, Dec. 20, 2012, pp. 345-350.
Marcati Alain et al., "Extraction and Fractionation of Polysaccharides and B-Phycoerythrin From the Microalga Porphyridium Cruentum by Membrane Technology", Algal Research-Biomass Biofuels and Bioproducts, vol. 5, Jul. 5, 2014, pp. 258-263.
Kadam S U et al., "Application of Novel Extraction Technologies for Bioactives From Marine Algae", Journal of Agricultural and Food Chemistry, American Chemical Society USA, vol. 61, No. 20, May 22, 2013, pp. 4667-4675.
Doucha J et al., "Influence of Processing Parameters on Disintegration of Chlorella Cells in Various Types of Homogenizers", Applied Microbiology and Biotechnology, Springer Berlin, DE, vol. 81, No. 3, Aug. 29, 2008, pp. 431-440.
Hongli Zheng et al., "Disruption of Cells for the Release of Biodiesel-Producing Lipids: A Comparison of Grinding, Ultrasonication, Bead Milling, Enzymatic Lysis, and Microwaves", Applied Biochemistry and Biotechnology; Part A: Enzyme Engineering and Biotechnology, Humana Press Inc., New York, vol. 164, No. 7, Feb. 24, 2011, pp. 1215-1224.
Li Zhang et al., "Releasing Polysaccharide and Protein From Yeast Cells by Ultrasound: Selectivity and Effects of Processing Parameters", Ultrasonics Sonochemistry Elsevier B.V. Netherlands, vol. 21, No. 2, pp. 576-581.
Nov. 26, 2015 Search Report issued in International Patent Application No. PCT/EP2015/073689.

* cited by examiner

*Primary Examiner* — Pancham Bakshi
(74) *Attorney, Agent, or Firm* — Oliff PLC

(57) ABSTRACT

A method for producing membrane polysaccharides from an organism selected from micro-organisms, unicellular organisms and filamentous fungi, the method including at least one step of extracting the membrane polysaccharides as well as a smaller-scale extraction of the soluble proteins, by mechanical treatment of the organism in a ball mill or by physical treatment of the organism by means of ultrasounds.

12 Claims, 4 Drawing Sheets

DEGUMMING METHOD

The present invention relates to the field of the exploitation of biomass, in particular algal biomass, more specifically the present invention relates to a process for extracting polysaccharides derived from microorganisms, in particular cyanobacteria, microalgae, bacteria, photosynthetic microorganisms and also filamentous fungi.

Microalgae are eukaryotic organisms, which are usually unicellular, and which are delimited by a plasma membrane and a wall. The composition and the structure of this wall may be variable depending on the microalga in question.

Thus, in certain green microalgae such as *Chlorella*, it consists of cellulose and is strongly rigid, giving the alga a high resistance to mechanical stresses.

For microalgae belonging to the diatom class, the wall, also called frustule, consists of crystalline silica. The latter is more brittle than that of *Chlorella*.

Finally, other species set out around their cell a polysaccharide coating in order to protect themselves against environmental attacks. The thickness of this coating varies over time; it is quite thin during exponential growth of the microalga, and then thicker in the stationary phase. In the stationary phase, the rate of production of membrane polysaccharides is higher than the rate of solubilization in the culture medium.

With the aim of exploiting all of the microalgal biomass, with biorefining being an objective, it is necessary to fractionate and to isolate the various metabolites of said microalgae which are generally soluble in the culture medium.

Thus, the main metabolites are polysaccharides, proteins and pigments.

The microorganisms more particularly targeted by the invention comprise several types of polysaccharides: intracellular polysaccharides and extracellular polysaccharides called membrane polysaccharides.

The microorganisms more particularly targeted by the invention are preferably unicellular.

However, for these polysaccharides, there is the problem of the extraction yield. This is because, during the culture of microalgae, some of the membrane polysaccharides are free, dissolved in the media. This free fraction may be easily recovered. However, there are also bound membrane polysaccharides, that is to say membrane polysaccharides attached to the outside of the cells, on their periphery. These bound membrane polysaccharides are sometimes called exopolysaccharides or EPSs.

In some species, such as *Porphyridium cruentum*, it is estimated that bound membrane polysaccharides constitute approximately 50% of all of the membrane polysaccharides.

The stated problem which is the origin of the present application lies in the difficulty in selectively extracting the membrane polysaccharides, that is to say in not only extracting the free membrane polysaccharides, but also in releasing the bound membrane polysaccharides into the medium without causing cell lysis.

More particularly, the stated problem which is the origin of the present application lies in the difficulty in extracting the bound membrane polysaccharides in the medium without causing cell lysis.

Indeed, this is because cell lysis results in releasing into the medium all or some of the cell constituents, which results in making the purification of the various metabolites, and in particular of the membrane polysaccharides, more complex.

It is known practice to extract polysaccharides from biomass, in particular from algae; for example, U.S. Pat. No. 4,960,697 discloses a process for extracting dissolved polysaccharides, in particular non-ionic glucans, using a divalent cation and then a water-miscible organic solvent in order to cause the polysaccharides to precipitate.

EP 0 311 496 describes a process for producing and extracting, chemically, pericellular and exocellular polysaccharides using a step of precipitating the polysaccharides, in particular with cetylpyridium.

WO 83/03738 describes a process for culturing a microalga of the *Porphyridium cruentum* strain and a process for extracting the membrane polysaccharides using the steps of basifying the solution by means of a concentrated sodium hydroxide solution, of heating, and of adding, under cold conditions, a hydrochloric acid solution. This hydrolysis is followed by precipitation of the polysaccharides by means of an organic solvent, in particular by adding from 2 to 3 volumes of ethanol.

This process allows the extraction of the intracellular and extracellular polysaccharides.

However, these processes cause destruction of the biomass, which is not compatible with the objective of exploitation of the various metabolites.

The process according to the invention allows the extraction of the bound membrane polysaccharides.

The process according to the invention thus allows the extraction of the membrane polysaccharides according to a high yield with a reduced degree of cell lysis.

Particularly, the invention is directed toward the extraction of polysaccharides derived from microalgae, cyanobacteria, bacteria, filamentous fungi, and photosynthetic microorganisms.

A first subject of the present invention is directed toward a process for obtaining membrane polysaccharides from an organism, said process comprising at least one step of extracting said membrane polysaccharides, accompanied by a reduced extraction of the soluble proteins, by mechanical treatment of said organism in a ball mill or by physical treatment of said unicellular organism by means of ultrasound.

More particularly, this process is directed toward the obtaining of the bound membrane polysaccharides.

The organisms targeted are more particularly selected from microorganisms, unicellular organisms and filamentous fungi.

Said mechanical or physical treatment may be carried out by any other technique which makes it possible to generate a sufficiently controlled mechanical stress on the cell. Mention may in particular be made of cavitation in a pipe which consists in generating a sufficient reduced pressure in the circulating culture to create the occurrence of bubbles generating a vibration wave having the expected mechanical effect.

A second subject of the invention is directed toward the uses of the soluble polysaccharide fraction obtained.

In greater detail, the invention is directed toward a process for obtaining membrane polysaccharides comprising the following steps, in this order:

providing a medium comprising at least one organism selected from microorganisms, unicellular organisms and filamentous fungi, performing, on said medium, a step of extracting said membrane polysaccharides, accompanied by a reduced extraction of the soluble proteins, by mechanical treatment of said organism in a ball mill or by physical treatment of said unicellular organism by means of ultrasound, extracting the soluble polysaccharide fraction from said medium, optionally purifying said fraction comprising the polysaccharides.

This process allows the extraction of the bound membrane polysaccharides.

Advantageously, the step of extracting said membrane polysaccharides is not accompanied by an extraction of the soluble proteins.

Preferably, this process is carried out in circuit mode.

For the purposes of the present invention, the expression "reduced extraction of the soluble proteins" is intended to mean that the selectivity of the extraction, defined as the ratio of the protein extraction yield to the EPS extraction yield, is less than 0.7.

The principle of the "circuit mode" used according to the present invention is presented in FIG. 1.

The circuit mode makes it possible to treat a volume "batchwise" on a continuous device in a simple manner.

According to this mode, the medium to be treated is placed in the feed vessel (A) where it is subjected to stirring and then sent to the reactor (R) where it is subjected to a treatment capable of increasing the concentration of soluble polysaccharides in this medium without increasing to such a high extent the concentration of soluble proteins of this medium. At the end of the treatment, the medium is sent back to the feed vessel where it is subjected to stirring. The medium to be treated is introduced N times into the reactor so as to be treated therein, which corresponds to the number of passes.

The assaying of the various metabolites produced during the treatment takes place in the feed vessel either at the end of the N treatments, or after each pass.

In the case where the assaying of the various metabolites is carried out after each pass, as long as the concentration of polysaccharides of the reaction medium increases, said medium is sent back to the reactor. The number of passes through the reactor is generally between 1 and 10, limits included.

The residence time of the composition corresponds to all of the passes of the composition through the reactor.

The process according to the invention makes it possible erode the cells and consequently to detach the fraction of bound membrane polysaccharides (or EPSs) without significantly modifying the integrity of the cells.

This treatment is also called degumming.

The process according to the present invention makes it possible, on the one hand, to increase the polysaccharide extraction yield compared with the prior art processes and, on the other hand, to facilitate the subsequent polysaccharide purification operations.

It has in fact been possible to increase the polysaccharide extraction yield so as to extract up to 90% by weight of membrane polysaccharides relative to the total weight of the membrane polysaccharides.

In addition, as already mentioned, the process according to the invention, insofar as it only modifies cell integrity, makes it possible to prevent other water-soluble constituents of the cell, for example water-soluble proteins and chlorophylls, from being released into the medium in too large an amount. It thus has the advantage of resulting in a reaction product that is less viscous than the products obtained by means of the prior art processes which result in cell lysis.

Indeed, from the viewpoint of biorefining the biomass, a selective extraction of each of the constituents of the cells is desired. However, selective extractions may be disrupted by the presence of certain compounds such as, in particular, the membrane polysaccharides which have a tendency to complex with other molecules of the medium such as proteins.

Thus, the process according to the invention makes it possible to increase the recovery yield and the purity of the water-soluble polysaccharides in the medium at the end of the reaction.

The component purification operations are facilitated in particular because of the reduced proportion of proteins in the recovered medium containing the polysaccharides, or else because of the removal of the polysaccharides from the cells, thus facilitating the downstream steps of recovery of other cell compounds capable of complexing the polysaccharides.

The process according to the invention should be considered as allowing a targeted and virtually total recovery of the free and bound membrane polysaccharides.

Another advantage of the process according to the invention is that it may be carried out directly on the culture medium of the organisms, in particular unicellular organisms, in particular on a suspension of microalgae at production output, thereby contributing to reducing the volumes of water used to carry out said process.

In addition, this process also makes it possible to avoid carrying out a drying step, which is by definition a long and expensive step, both in energy terms and in financial terms.

According to one variant of the process according to the invention, the mechanical or physical treatment step is followed by a step of measuring the amount of membrane polysaccharides extracted.

The process according to the invention may comprise a plurality of treatment steps, advantageously from 2 to 10 treatment steps.

The process according to the invention may also comprise at least one mechanical or physical treatment step, followed by a step of measuring the amount of membrane polysaccharides extracted.

Any method which makes it possible to determine the amount of membrane polysaccharides extracted may be implemented.

These methods are part of the general competence of those skilled in the art, such as colorimetric methods.

In particular, the assaying of the polysaccharides is carried out by means of the colorimetric method using phenol and sulfuric acid (Dubois M, Gilles K A, Hamilton J K, Rebers P A, Smith F. Colorimetric method for determination of sugars and related substances. *Anal. Chem.* 1956; 28:350-356).

According to another variant, the process according to the invention may also comprise a plurality of treatment steps, with at least two treatment steps which are each followed by a step of measuring the amount of membrane polysaccharides that have been extracted.

In particular, said process may be interrupted when the amount of membrane polysaccharides measured at the end of a treatment step N is substantially identical to the amount of membrane polysaccharides measured at the end of a treatment step N–X, X being a number of treatments lower than the total number of treatments N, in particular X is equal to 1.

Advantageously, the process according to the invention comprises a step consisting in extracting the soluble polysaccharide fraction from said medium.

Advantageously, the step of extracting the membrane polysaccharides is followed by a step of purifying said polysaccharides.

In the process according to the invention, the step of extracting the membrane polysaccharides may be followed by a step of purifying said polysaccharides.

It is part of the competence of those skilled in the art to select the suitable purification process; this process will conventionally be selected from the pH-change methods, the ethanol precipitation methods, and physical separations using a membrane.

The process for extracting polysaccharides according to the invention may be carried out from any organism, preferably microorganism; it is preferably carried out from cyanobacteria, microalgae, bacteria, or filamentous fungi.

Advantageously, the process according to the invention is carried out during the stationary phase of the microalga, that is to say in an intermediate or mature physiological state, at the end or after the "exponential growth" phase.

Preferably, the organism is selected from: the division Rhodophyta and more specifically from the genera *Porphyridium* and *Rhodella*, *Spirulina* and *Dunaliella*, and preferably from the following strains: *Porphyridium cruentum*, *Arthospira platensis*, *Botryococcus braunii*, *Criptecodinium conhii*, *Chlorella autotrophica*, *Navicula incerta* and *Rhodosorus marinus*.

Process Using a Ball Mill

According to a first preferred variant, the process according to the invention comprises a step during which a ball mill is used.

Ball mills are conventionally used for homogenizing viscous products such as paints and also for milling minerals. Ball mills comprise a chamber, for example a bowl closed by a lid, intended to receive the composition to be treated, said chamber being fed, via a pump, with composition to be treated.

Conventionally, the filling rate, corresponding to the percentage of the volume of the bowl occupied by the balls, of the ball mill ranges from 50% to 80%, preferably from 65% to 80%.

The content of the chamber, excluding balls, essentially comprises the unicellular organism or the suspension to be treated.

The filling rate may be adjusted in particular according to the nature of the balls used. Indeed, in certain cases, it has been possible to observe an agglomeration of the balls between the blades of the stirrer.

In the case of balls, in particular made of glass, the ball filling rate of the mill advantageously ranges from 60% to 80% and preferably from 65% to 80% volume/volume.

It is part of the competence of those skilled in the art to select the filling rate suitable for the medium to be treated.

The feed flow rate of the composition in the mill generally ranges from 150 ml/min to 200 ml/min. It is also part of the competence of those skilled in the art to select the feed flow rate suitable for the medium to be treated.

The treatment with the ball mill is generally carried out at a temperature included from 18 to 40° C., preferably from 18 to 25° C.

According to a first variant of the process, the mechanical treatment used in the process according to the invention uses a glass ball mill under the following conditions:
the mean diameter of the balls ($d_{GM}$) ranges from $1.5 \times 10^{-3}$ to $2.5 \times 10^{-3}$ m,
the stirring speed at the blade end (v) ranges from 5 to 20 m·sec$^{-1}$.

At the end of the ball milling step, the composition treated is recovered and then the polysaccharides present in said composition are extracted and optionally purified.

According to one implementation of the process, a single ball milling step is carried out.

According to one preferred implementation of the process, the treatment in a ball mill is repeated at least twice, preferably between two and ten times and advantageously between three and four times.

Preferably, the treatment in a ball mill is carried out for a residence time ranging from 2 to 50 minutes, preferably from 10 to 40 minutes.

Process Using Ultrasound

According to this process, the medium to be treated is pumped through the ultrasound reactor within which it will undergo the ultrasound treatment.

According to a second variant of the process, the physical treatment uses an ultrasound reactor under the following conditions:
the energy ranges from 500 to 5000 J,
the power ranges from 200 to 400 W,
the feed flow rate of the reactor ranges from 0.150 l/min to 3 l/min.

At the end of the ultrasound treatment step, the composition treated is recovered and then the polysaccharides present in said composition are extracted and optionally purified.

Preferably, the mechanical treatment with ultrasound is carried out for a period ranging from 5 to 30 seconds.

Properties of the Membrane Polysaccharides

The present invention is also directed toward the uses of the soluble polysaccharide fraction obtained according to the process according to the invention, said process comprising a step consisting in extracting the soluble polysaccharide fraction from said medium, optionally followed by a step of purifying said polysaccharides.

Said membrane polysaccharide fraction is used in chemical, food, cosmetic or pharmaceutical compositions.

Said membrane polysaccharide fraction has advantageous properties, in particular texturing properties.

It may be used as thickeners, gelling agents, surfactants or else stabilizers of compositions and more particularly of emulsions.

It may thus be used in phytosanitary products or as phytosanitary products.

Said membrane polysaccharide fraction may also be used as materials, in particular adhesives.

The membrane polysaccharides obtained according to the invention may also be fractionated into oligosaccharides.

The oligosaccharides thus obtained are advantageously used as reactants in fine chemistry.

Figure 3:
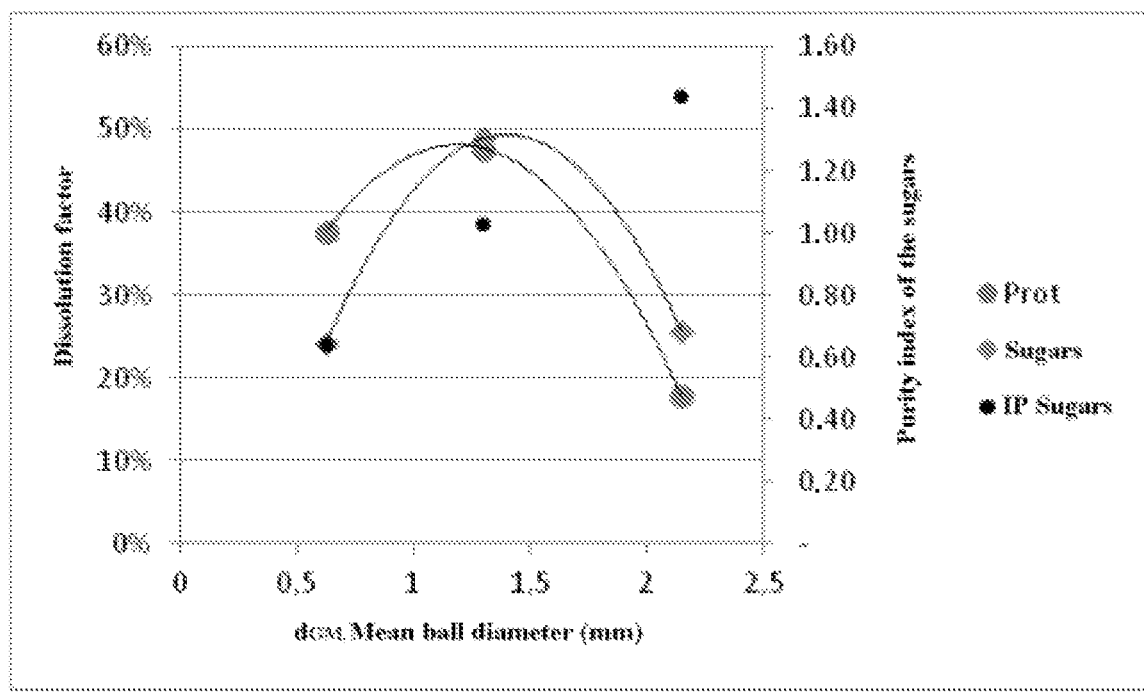

Represented in FIG. 3 are, on the one hand, the curves of the factors of dissolution of the proteins and of the polysaccharides and, on the other hand, the purity index (IP) of the sugars, as a function of the mean ball diameter.

Figure 4:
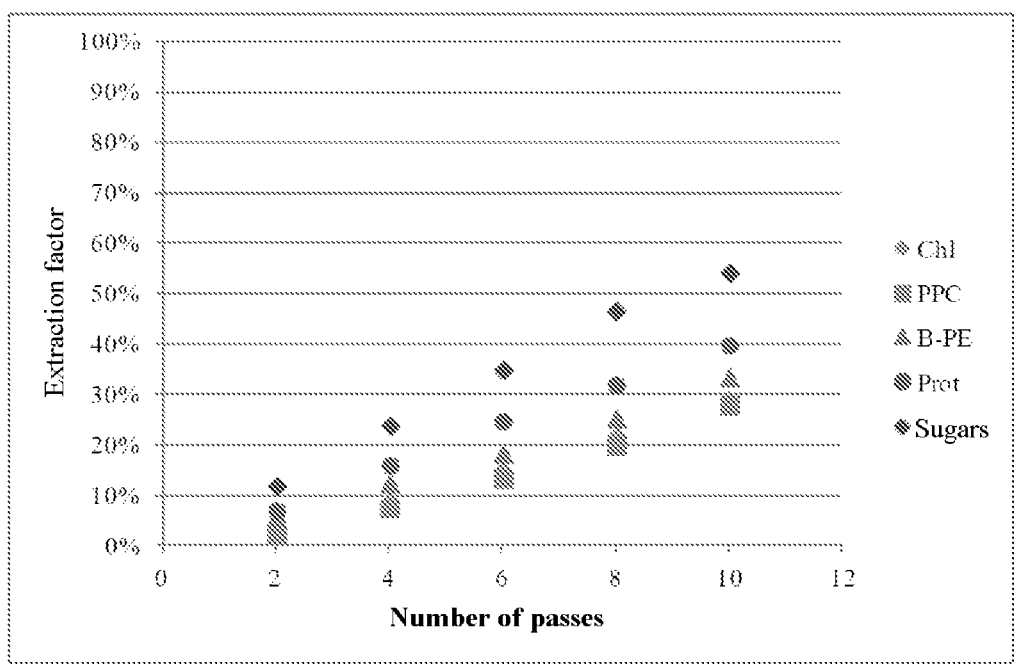

FIG. 4 represents the ultrasound extraction factor on a young biomass as a function of the number of passes at 2000 J (200 W).

Figure 5:
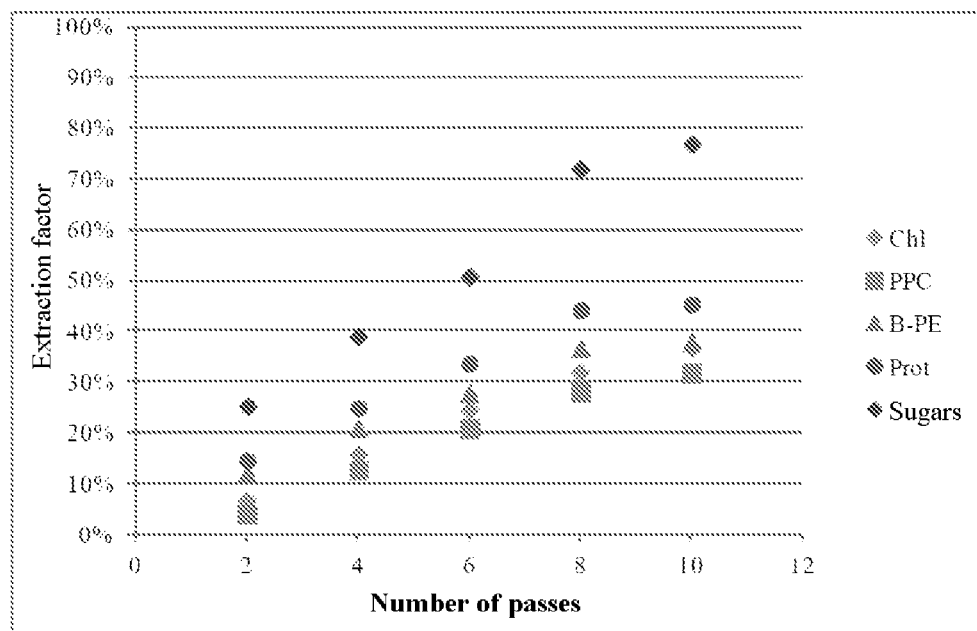

FIG. 5 represents the ultrasound extraction factor on an intermediate-aged biomass as a function of the number of passes at 2000 J (200 W).

Figure 6:
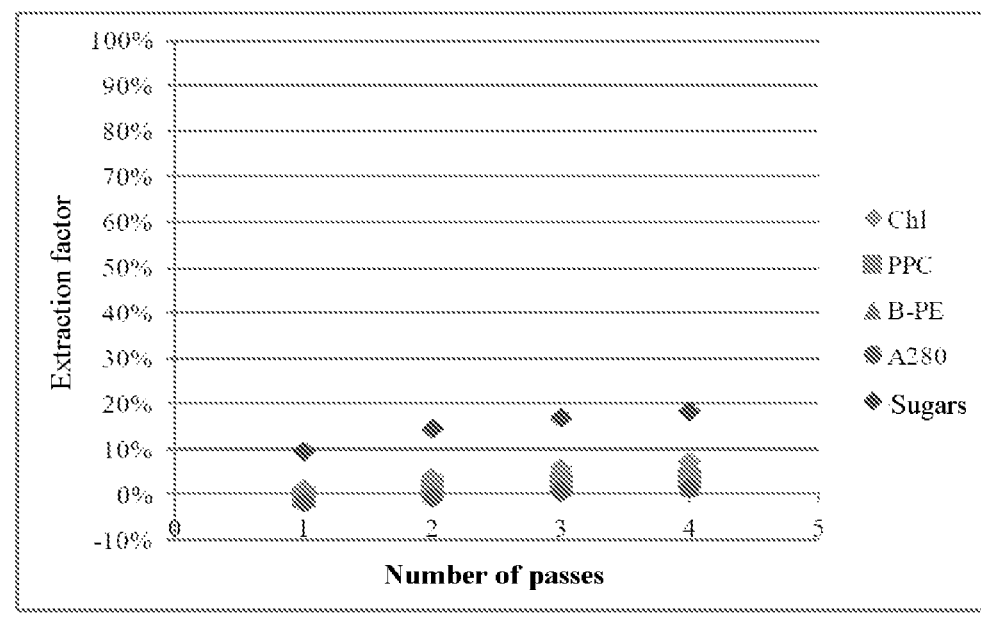

FIG. 6 represents the ultrasound extraction factor on a mature biomass as a function of the number of passes at 2000 J (400 W).

Figure 7:
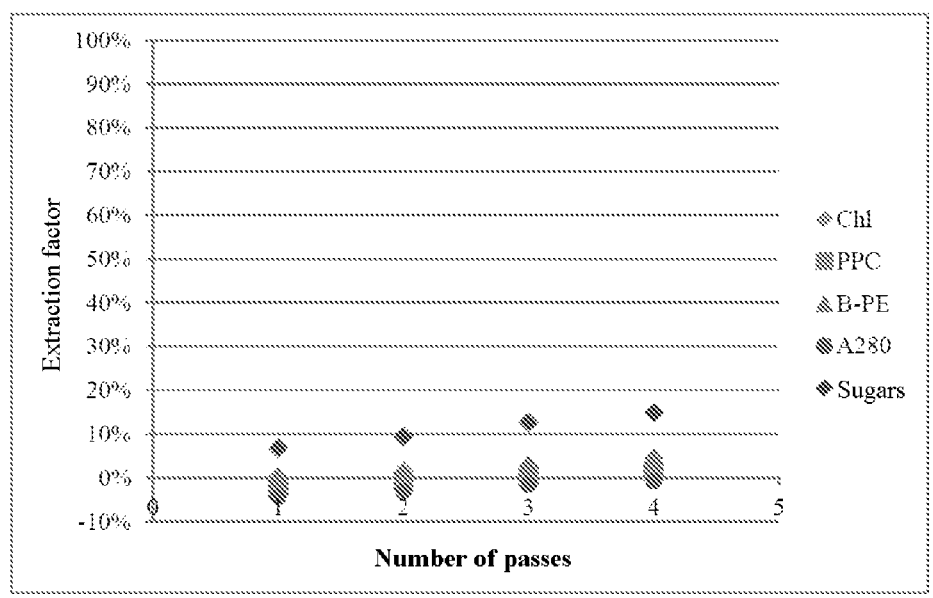

FIG. 7 represents the ultrasound extraction factor on a mature biomass as a function of the number of passes at 2000 J (200 W).

The examples which follow illustrate the invention without limiting the scope thereof.

EXAMPLES

For all these examples, a *Porphyridium cruentum* culture medium is used. This biomass was cultured in a 10 l tubular photobioreactor.

The proteins (denoted "prot" in the figures) are measured by absorbance at 280 nm, said measurement being optionally supplemented by a protein assay carried out according to the BCA protocol in order to verify the accuracy of the spectrophotometric measurements.

The quantification of the pigments: total chlorophylls and total carotenoids (denoted respectively Chi and PPC in the figures) is carried out by spectrometry respectively at 678 nm and 416 nm.

The B-Phycoerythrin (denoted B-PE in the figures) is assayed by the Bermejo protocol.

1. Process Using a Ball Mill 1.1 Example: Determination of the Extraction Factor as a Function of the Mean Bead Diameter The *Porphyridium cruentum* culture medium was treated by means of a glass ball mill (DynoMill Mutlilab, WAB, Switzerland) under the following conditions:

Q: feed flow rate in ml/min: 170

$\varphi$: mill filling rate: 75% n: stirring speed: 2389 min$^{-1}$→v: speed at stirrer blade end 8 m·sec$^{-1}$.

By way of reference, a High Pressure mill (2700b) enables cell destruction and consequently the release of all (100%) the metabolites in solution/stable suspension, thus of all the polysaccharides, is carried out. The unit of measurement for each metabolite will be the extraction factor, the maximum (100%) of which corresponds to the response obtained with the HP milled material.

After the milling step(s), a centrifugation is carried out (13 400×g, 10 min), and the analyses are carried out on the supernatant constituting the microalgae aqueous extract.

Figure 1:
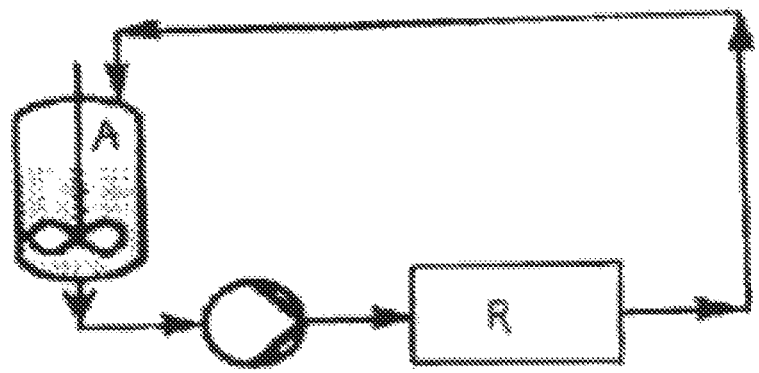
FIG. 1 presents the principle of the circuit mode detailed above.
Figure 2:
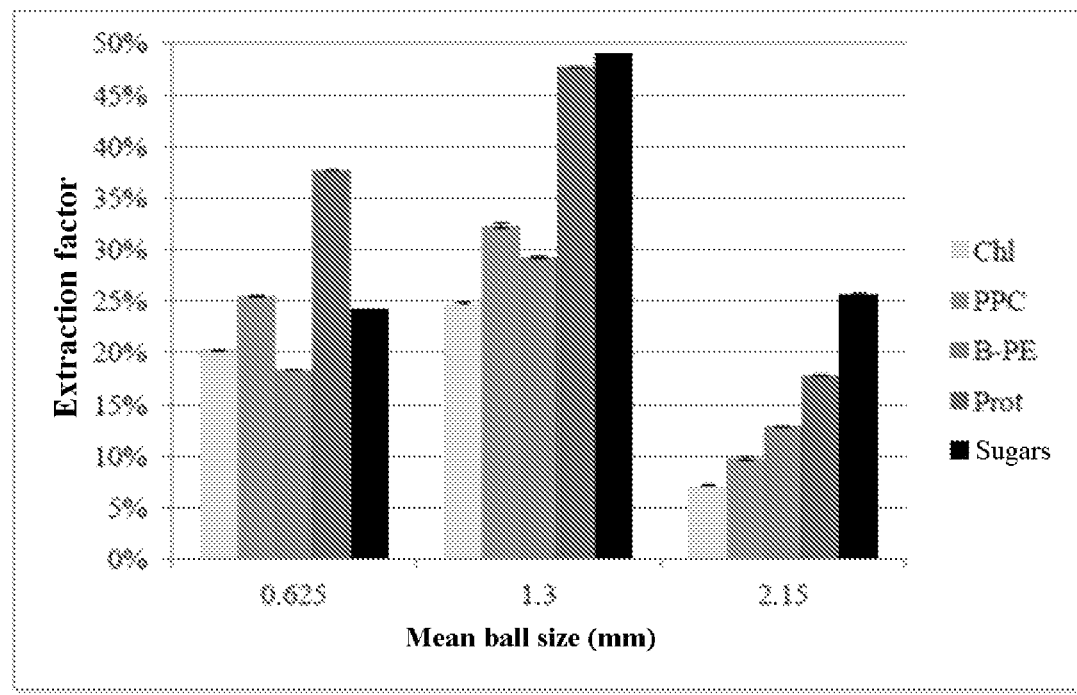
FIG. 2 represents the extraction factor as a function of the mean ball size.

The results are presented in FIG. 2.

Three milling treatments were carried out with balls having a different mean diameter:

a) with balls having a mean diameter of 0.625×10$^{-3}$ m, deconstruction of the cells is observed, the protein selectivity is at the maximum. The balls are not suitable for recovering the polysaccharides. During the deconstruction of the cells, the cell compartmentalization is respected, the release of the metabolites is generally selective;

b) with balls having a mean diameter of 1.3×10$^{-3}$ m, destruction which is similar to cell disintegration is observed (the cell is completely destructured, the debris is fine), and is accompanied by release of the proteins, of the polysaccharides and also of the pigments in a homogeneous manner. The homogeneous release of all the pigments reflects an extreme destruction of the cell; this process is less selective between proteins and polysaccharides, it does not allow selective extraction of the polysaccharides.

c) the balls having a mean diameter of 2.15×10$^{-3}$ m are the most suitable for the selective extraction of the sugars compared with the cell metabolites; this process is the one which results in the least cell destruction.

1.2 Determination of the Dissolution Factors and Purity Index

On the basis of the results obtained at the end of the three milling operations above, the curves of the dissolution factors of the proteins and of the polysaccharides were plotted, as a function of the mean ball diameter, in FIG. 3 and on the same graph, the purity index of the sugars was plotted.

It emerges from this graph that, starting from a mean ball diameter of 1.3×10$^{-3}$ m, the dissolution factor of the polysaccharides is greater than the dissolution factor of the proteins and that the purity index of the polysaccharides increases with the size of the balls.

Selecting balls having a mean diameter greater than 1.5×10$^{-3}$ m provides conditions under which the degree of dissolution of the membrane polysaccharides is greater than that of the other cell compounds, in particular the proteins.

Selecting balls having a mean diameter equal to 2.15×10$^{-3}$ m provides conditions under which the degree of dissolution of the membrane polysaccharides is low, but under which the purity index is higher.

By performing several passes of the medium to be treated through the ball mill, with balls having a mean diameter of greater than 1.5×10$^{-3}$ m, dissolutions of the order of 80% are successfully obtained.

2. Process Using Ultrasound

The technology used is the Sonitube® Type SM 35/3, supplied by Synetude It is an ultrasound tunnel which has a maximum power of 400 W, the operating frequency of which is 35 kHz.

The suspension is pumped through the Sonitube, in which it will be subjected to the ultrasound treatment (volume of 70 ml of treatment volume). The operating parameters are thus the feed flow rate and also the ultrasound power (200 W-400 W). During operation, a significant part of the energy supplied to the fluid is dissipated in the form of heat. As a result, the temperature of the suspension will be monitored, so that it does not exceed 30° C.

During each experiment, the HP milling carried out at 2700b defined in the preceding paragraph serves as a reference.

Following the sonication step, a centrifugation is carried out (13 000×g, 10 min).

All the analyses will be carried out on the supernatant, constituting the microalgae aqueous extract.

For the ultrasound, batchwise tests were carried out.

Biochemical protein assays were carried out in order to dispense with the potential bias that the extraction factor calculated from the $A_{280}$ might have.

On the basis of the finding that, in the stationary phase, the level of production of membrane polysaccharides is greater than the level of dissolution in the culture medium, it was decided to carry out the ultrasound treatment on suspensions of *Porphyridium cruentum* of which the physiological state differs.

This is because, in the young physiological state, the level of production of membrane polysaccharides is still low and in any event lower than the level of dissolution in the culture medium.

a. Young Physiological State

The culture was at 3.7 g solids/l, including 1.5 g/l of bound membrane polysaccharides and 0.3 g/l of dissolved membrane polysaccharides. The monitoring during the successive passes is presented in FIG. 4.

A certain selectivity is observed. The ultrasound treatment makes it possible to achieve a release of more than 50% of the bound membrane polysaccharides, with a protein release of the order of 40%. Nevertheless, the physiological state of the cells means that the degumming takes place on a relatively small amount of the bound membrane polysaccharides (1.5 g/l).

This physiological state may also explain the high level of cell destruction.

b. Intermediate Physiological State, Beginning of Stationary Phase

The culture was at 4.5 g solids/l, including 1.7 g/l of bound membrane polysaccharides and 0.4 g/l of dissolved membrane polysaccharides. The monitoring during the successive passes is presented in FIG. 5.

As the culture ages, the amount of bound EPSs increases. The selective degumming phenomenon appears to be promoted with the increase in bound membrane polysaccharides. Indeed, it is possible to achieve a very satisfactory membrane polysaccharide extraction factor (close to 80%) while limiting the release of soluble proteins (<50%). The thickness of the cell wall of *Porphyridium cruentum* during its maturation thus appears to make it possible to detach a greater part thereof without however systematically lysing the cells.

c. Mature Physiological State

The culture was at 6.4 g solids/l, including 3.2 g/l of bound membrane polysaccharides and 0.44 g/l of dissolved membrane polysaccharides. For this experiment, the minimum and maximum operating powers were tested, namely 200 W and 400 W. The monitorings during the successive passes are presented in FIGS. 6 and 7.

A very weak cell lysis is observed (<5%) on this biomass. While the reliability of $A_{280}$ may be contested (some values around 0%), the B-PE assay is a method acknowledged to be reliable and may thus serve as an indicator of (extreme) lysis.

In this context, it would appear that the treatment at 400 W is more selective than that at 200 W. Indeed, the ratio of the extraction factors [polysaccharides (%)]/[B-PE (%)] is 3.5 at 200 W and 8 at 400 W. Furthermore, a more extensive degumming is observed at 400 W (close to 20%).

It emerges from these experiments that ultrasound under appropriate conditions enables degumming of the microalga.

The invention claimed is:

1. A process for obtaining membrane polysaccharides from an organism selected from microorganisms, unicellular organisms and filamentous fungi, wherein the process comprises at least one step of extracting the membrane polysaccharides, accompanied by a reduced extraction of the soluble proteins, by mechanical treatment of the organism in a ball mill or by physical treatment of the organism by means of ultrasound, and wherein:

the process is performed by mechanical treatment using a ball mill equipped with glass balls under the following conditions:
a mean diameter of the balls ($d_{GM}$) ranges from $1.5 \times 10^{-3}$ to $2.5 \times 10^{-3}$ m, and
a stirring speed at a blade end (v) ranges from 5 to 20 m·sec$^{-1}$, or the process is performed by physical treatment by means of ultrasound under the following conditions:
an energy of the ultrasound ranges from 500 to 5000 J,
a power of the ultrasound ranges from 200 W to 400 W, and
a feed flow rate ranges from 0.150 l/min to 3 l/min.

2. The process as claimed in claim 1, wherein the process is performed by the mechanical treatment using the ball mill equipped with glass balls.

3. The process as claimed in claim 2, wherein the mechanical treatment using the ball mill is carried out for a period ranging from 2 to 50 minutes.

4. The process as claimed in claim 2, wherein a ball filling rate of the mill ranges from 60% to 80% volume/volume.

5. The process as claimed in claim 1, wherein the process is performed by the physical treatment using ultrasound.

6. The process as claimed in claim 5, wherein the ultrasound treatment is carried out for a period ranging from 5 to 30 seconds.

7. The process as claimed in claim 1, wherein the mechanical or physical treatment step is followed by a step of measuring an amount of membrane polysaccharides extracted.

8. The process as claimed in claim 1, wherein at least one treatment step is followed by a step of measuring an amount of membrane polysaccharides that have been extracted.

9. The process as claimed in claim 1, wherein the organism is selected from cyanobacteria, microalgae, bacteria and filamentous fungi.

10. The process as claimed in claim 1, wherein the organism is selected from: the division Rhodophyta and from the genera *Porphyridium* and *Rhodella*, *Spirulina* and *Dunaliella*.

11. The process as claimed in claim 1, wherein it comprises a step consisting in extracting the soluble polysaccharide fraction from a medium.

12. The process as claimed in claim 1, wherein the membrane polysaccharide extraction step is followed by a step of purifying the polysaccharides.

* * * * *